United States Patent
Vaucher et al.

(10) Patent No.: US 10,213,242 B2
(45) Date of Patent: Feb. 26, 2019

(54) FASTENING DEVICE AND TOOL FOR SURGICAL HOLDING SYSTEMS

(71) Applicant: Creaholic S.A., Biel (CH)

(72) Inventors: Vincent Vaucher, Eschert (CH); Markus A. Muller, Zurich (CH)

(73) Assignee: CREAHOLIC S.A., Biel (CH)

( * ) Notice: Subject to any disclaimer, the term of this patent is extended or adjusted under 35 U.S.C. 154(b) by 1126 days.

(21) Appl. No.: 14/376,520

(22) PCT Filed: Feb. 5, 2013

(86) PCT No.: PCT/CH2013/000022
§ 371 (c)(1),
(2) Date: Oct. 6, 2014

(87) PCT Pub. No.: WO2013/116952
PCT Pub. Date: Aug. 15, 2013

(65) Prior Publication Data
US 2015/0045840 A1  Feb. 12, 2015

(30) Foreign Application Priority Data

Feb. 6, 2012 (EP) .................................. 12405017

(51) Int. Cl.
| | |
|---|---|
| A61B 17/80 | (2006.01) |
| A61B 17/86 | (2006.01) |
| A61B 17/17 | (2006.01) |
| A61B 17/88 | (2006.01) |
| A61B 17/00 | (2006.01) |
| A61B 90/00 | (2016.01) |

(52) U.S. Cl.
CPC ...... *A61B 17/8685* (2013.01); *A61B 17/1728* (2013.01); *A61B 17/8038* (2013.01); *A61B 17/8042* (2013.01); *A61B 17/8047* (2013.01); *A61B 17/8605* (2013.01); *A61B 17/8875* (2013.01); *A61B 2017/00004* (2013.01); *A61B 2090/031* (2016.02)

(58) Field of Classification Search
CPC ............ A61B 17/8685; A61B 17/8028; A61B 17/8033; A61B 17/8047; A61B 2017/868
USPC .................................................. 606/286–290
See application file for complete search history.

(56) References Cited

U.S. PATENT DOCUMENTS

| | | | |
|---|---|---|---|
| 5,464,407 A | 11/1995 | McGuire | |
| 8,734,495 B2 * | 5/2014 | Black ................. | A61B 17/8047 606/290 |

(Continued)

FOREIGN PATENT DOCUMENTS

| | | |
|---|---|---|
| EP | 1346697 | 9/2003 |
| WO | 20091017656 | 2/2009 |

*Primary Examiner* — Matthew Lawson
(74) *Attorney, Agent, or Firm* — Rankin, Hill & Clark LLP

(57) ABSTRACT

A fastening device for surgical holding systems includes a holding element and a fastening element with a ball joint, which can be locked by way of rotating an eccentric ring in the holding element. The joint socket defines a joint inner surface of the ball joint and the joint head a joint outer surface of the ball joint. When the eccentric ring clamps the joint head with respect to the joint socket, the position of three contact locations of the ball joint which lock the ball joint are unambiguously defined due to the shape of at least one of the three elements: joint socket, joint head and eccentric ring.

20 Claims, 7 Drawing Sheets

(56) References Cited

U.S. PATENT DOCUMENTS

| | | | |
|---|---|---|---|
| 2003/0225409 A1* | 12/2003 | Freid | A61B 17/7059 606/281 |
| 2004/0019353 A1* | 1/2004 | Freid | A61B 17/1728 606/915 |
| 2005/0277940 A1 | 12/2005 | Neff | |
| 2006/0264936 A1 | 11/2006 | Partin | |
| 2008/0243192 A1* | 10/2008 | Jacene | A61B 17/8047 606/290 |
| 2009/0149888 A1* | 6/2009 | Abdelgany | A61B 17/7059 606/286 |
| 2010/0069969 A1* | 3/2010 | Ampuero | A61B 17/8605 606/301 |
| 2010/0256686 A1* | 10/2010 | Fisher | A61B 17/8047 606/286 |
| 2011/0022096 A1* | 1/2011 | Cummins | A61B 17/8047 606/279 |
| 2011/0093016 A1* | 4/2011 | Aferzon | A61B 17/8042 606/279 |
| 2011/0182693 A1* | 7/2011 | Helgerson | A61B 17/7064 411/337 |
| 2012/0022600 A1 | 1/2012 | Overes | |
| 2012/0089192 A1* | 4/2012 | Biedermann | A61B 17/1728 606/280 |
| 2013/0190825 A1* | 7/2013 | Perrow | A61B 17/8042 606/281 |

\* cited by examiner

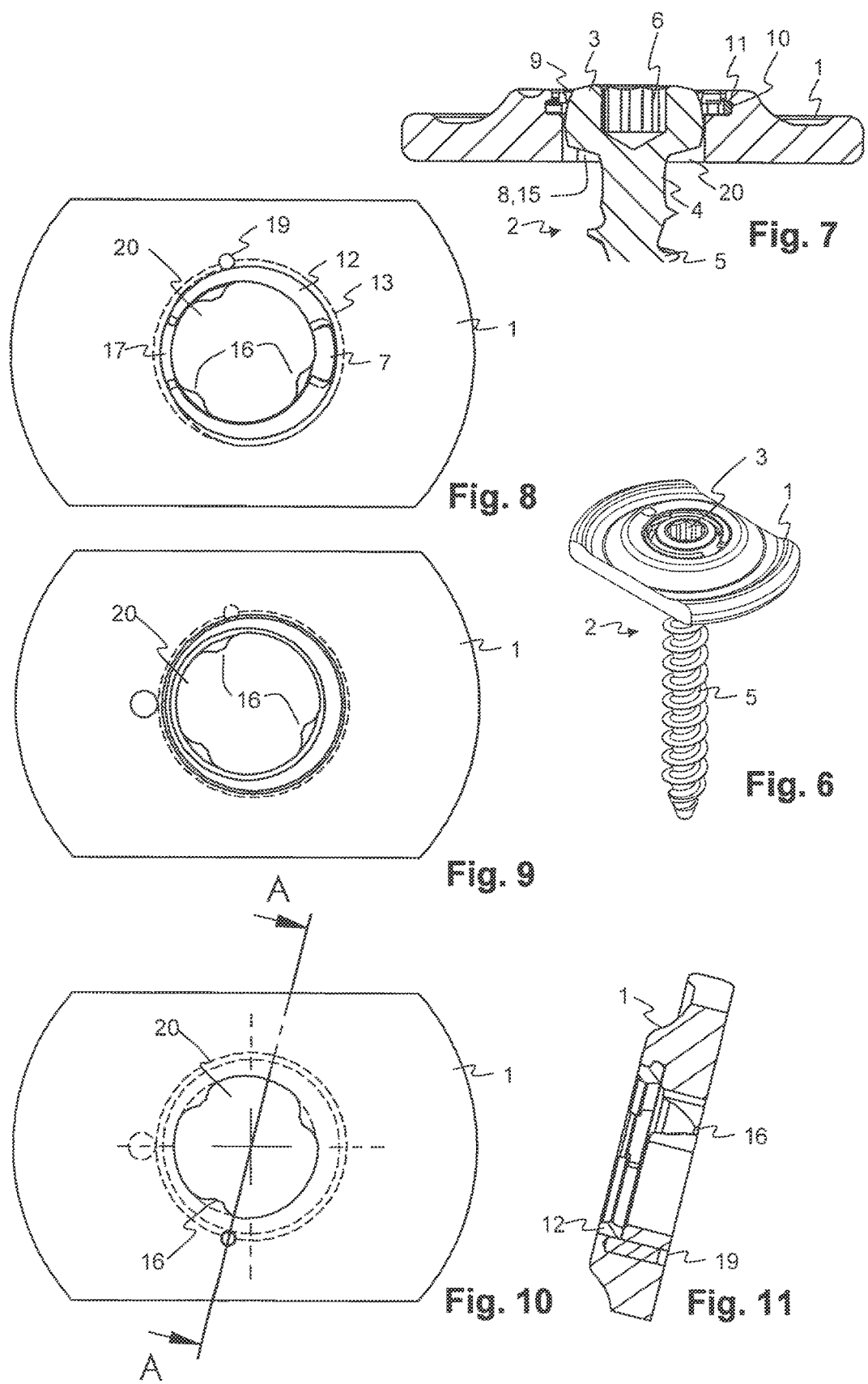

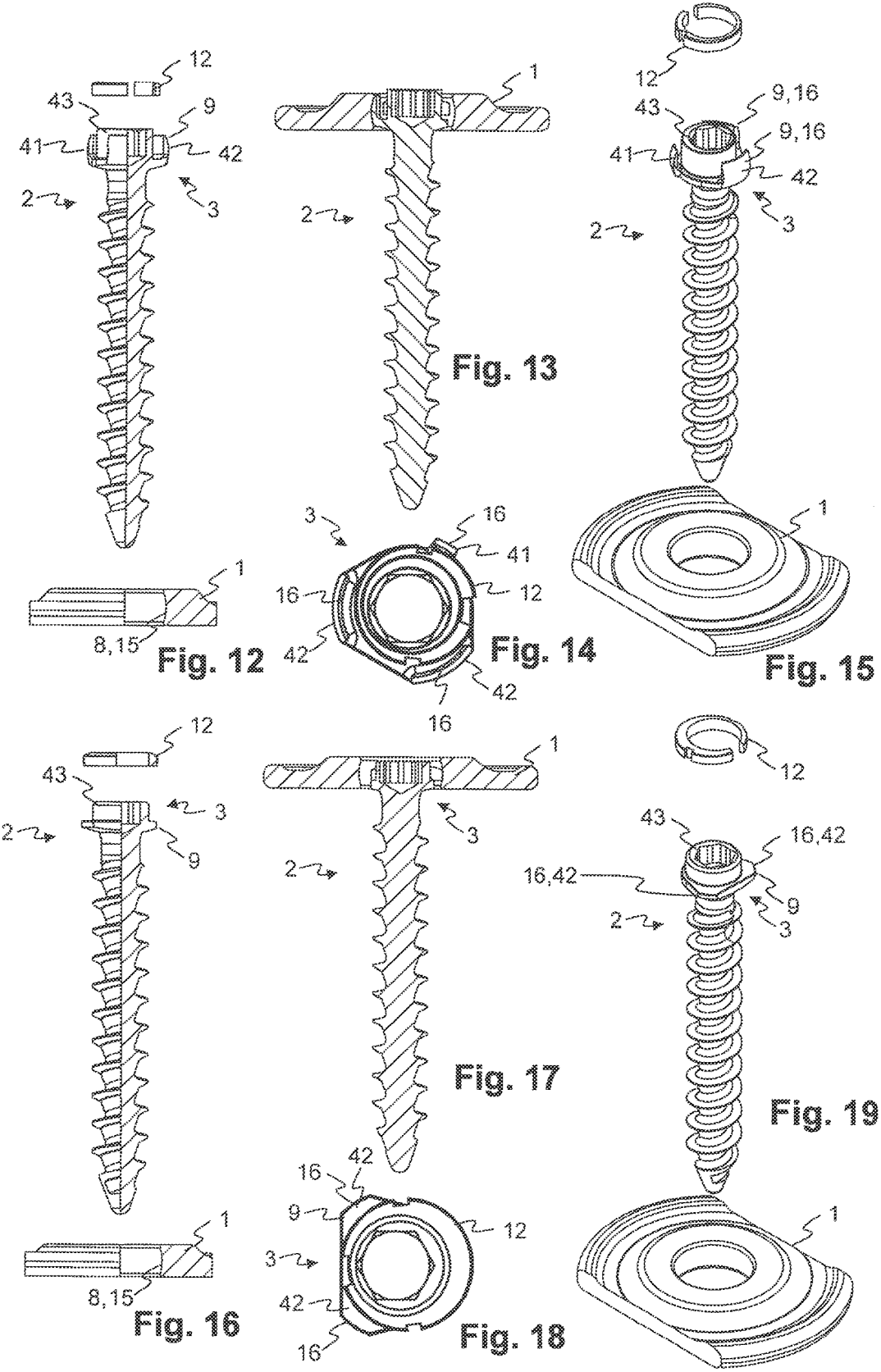

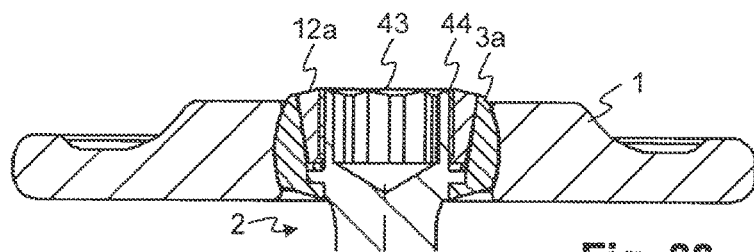
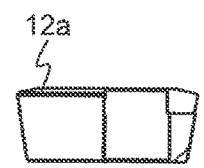
Fig. 20
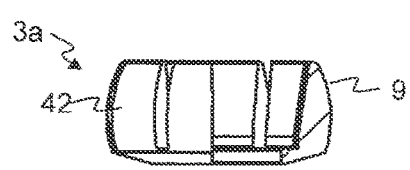
Fig. 21
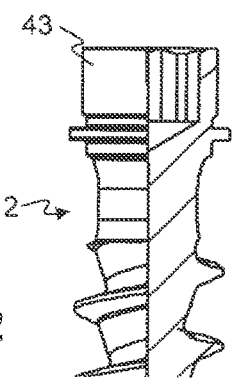
Fig. 24
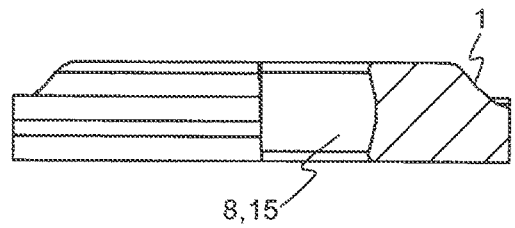
Fig. 22
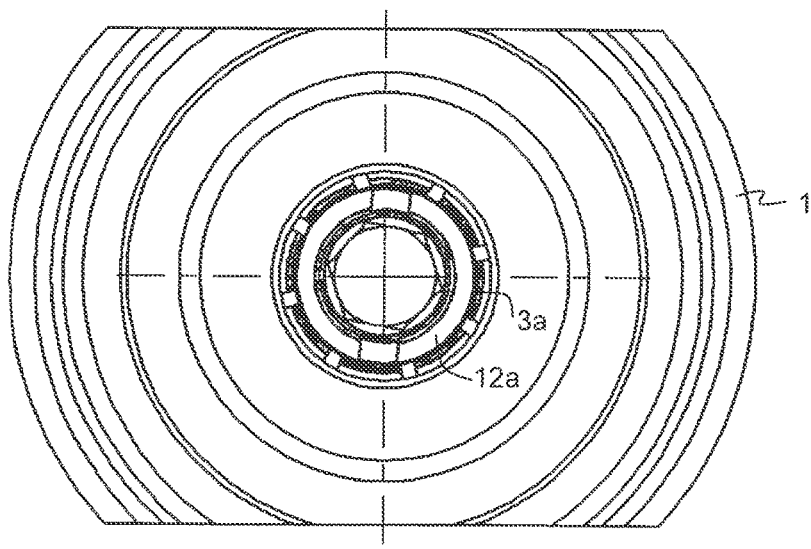
Fig. 23

FASTENING DEVICE AND TOOL FOR SURGICAL HOLDING SYSTEMS

BACKGROUND OF THE INVENTION

Field of the Invention

The invention relates to the field of surgical holding systems and in particular to a fastening device for surgical holding systems, to a surgical holding element and to a tool for surgical holding systems.

Description of Related Art

Surgical holding systems, for example for fixing broken bones, often consist of plates that are fastened into the bone by way of screws. The plates comprise openings, into which the screws are inserted at different angles. A surgical holding system is known from WO 2010/121388 A1, which is owned by the present applicant, with which a joint head of a screw with a joint socket in a plate forms a ball joint. The orientation of the screw in the joint socket is fixable by way of an eccentrically designed clamping ring. The clamping ring for this is rotatably mounted in the plate and on rotation clamps against the joint head of the screw.

Thereby, the problem of exactly two contact points between the joint head on the one hand and the joint socket and the clamping ring on the other hand results with the clamping, due to the geometry of the ball joint and the clamping ring. This is a consequence of the non-ideal shape of these parts due to manufacturing tolerances. Although it is then possible for the parts to plastically deform by way of continued, heavy tensing of the clamping ring, and for further contact points to arise, however, if this does not happen then the two contact points define an axis, about which the joint head can rotate with respect to the joint socket, so that the connection is not correctly locked (arrested) under all circumstances.

SUMMARY OF THE INVENTION

It is therefore the object of the invention, to provide a fastening device for surgical holding systems, and a surgical holding instrument of the initially mentioned type, which overcome the disadvantages mentioned above.

A further object of the invention to create a tool, with which the fastening device can be locked or released in a secure and simple manner, and also the screw can be screwed in or screwed out.

In accordance with the present invention, the fastening device, provided for surgical holding systems, includes at least one holding element and a fastening element that can be mechanically connected to one another. The holding element includes a joint socket, and the fastening element includes a joint head. The joint socket and the joint head preferably, at least in sections, with regard to their shape correspond to one another and together form a ball joint. The movement of the ball joint can be locked via a clamping element. The clamping element of the fastening device includes a ring with an eccentric shape, which on rotation of the ring clamps and/or tenses the joint head with respect the joint socket. The joint socket and a ring inner surface of the eccentric ring together define a joint inner surface of a joint shell (socket), in which the joint head is mounted, wherein an outer ball surface of the joint head lies opposite the joint inner surface. Thereby, when the eccentric ring clamps the joint head with respect to the joint socket, the position of three contact locations of the ball joint, which lock the ball joint, is unambiguously defined due to the shape of at least one of the three elements—the joint socket, the joint head and the eccentric ring.

It is noted that the inventive arrangement is in sharp contrast to connection systems wherein, for example, a smooth surface or one which is grooved, profiled or structured in another manner is present on the joint inner surface and/or the ball surface. Such surfaces lead to a multitude of contact locations whose position, however, is subject to chance and thus not unambiguously defined. With the fastening device according to the present invention, in contrast, there are at least three contact locations, but this does not exclude yet a fourth unambiguously defined contact location being present under certain geometric conditions, without a deformation on these parts having taken place. Moreover, it also does not exclude further contact locations arising with an increasing clamping, whose position however is not defined.

On account of this, it is possible to screw the screws into the bone at a relatively freely selectable angle, and, independently of the exact position of the screws, to lock these with the plate in an angularly stable manner thanks to the three-point connection between the joint socket (with clamping element) and the joint head.

The eccentric ring—irrespective of whether it is rotatably arranged on the holding element or on the fastening element—as a rule on the one hand itself is eccentrically mounted with respect to the center of the ball joint, thus rotatable about an axis which does not lead through this center. On the other hand, an inner surface of the ring which essentially follows a cylindrical shape and which, at least in sections or in a pointwise manner, is in contact with the fastening element, and outer surface of the ring which follows an essentially cylindrical shape and which at least in sections or in a pointwise meaner is in contact with the holding element, are not concentric to one another.

According to one variant of the fastening device, envisaged for surgical holding systems, it comprises at least one holding element and a fastening element, which can be mechanically connected to one another. The holding element includes a joint socket, and the fastening element a joint head. The joint socket and the joint head preferably, at least in sections, correspond to one another in their shape, and together form a ball joint. The movement of the ball joint is lockable by way of a clamping element. The clamping element of the fastening device comprises a ring with an eccentric shape, which on rotation of the ring clamps and/or tenses the joint head with respect to the joint socket. The joint socket and a ring inner surface of the eccentric ring together define a joint inner surface of a joint shell (socket), in which the joint head is mounted, wherein an outer ball surface of the joint head lies opposite the joint inner surface. Thereby:

either the joint inner surface comprises exactly two or exactly three inwardly projecting contact regions, or the joint outer surface comprises exactly two or exactly three outwardly projecting contact regions, wherein when the eccentric ring clamps the joint head with respect to the joint socket, but no deformation on these parts has taken place, exactly three contact locations or also exactly four contact locations are present between the joint inner surface and the joint outer surface.

With regard to terminology, it is to be noted that as a rule the term "contact region" (mostly as a projecting contact region) stands for a design of the element that is given by the shape of an element—thus the joint socket, joint head or clamping element—and, thus, which is also recognisable on the element itself. The term "contact location" in contrast indicates points or regions in which the elements lie on one another and the greatest forces are transmitted or occur when clamping. As to where exactly the contact locations occur is dependent on the mutual arrangement of the elements and on the position of their contact regions. Some of the contact regions become contact locations. Conversely, some contact locations result at contact regions, and other contact locations typically result by way of one or in particular two contact regions pressing onto the elements from an opposite side of the joint.

In one embodiment, the eccentric ring is rotatably arranged on the holding element and on rotation of the eccentric ring with respect to the holding element, the eccentric ring itself or an intermediate element moved by the eccentric ring is pressed against the joint outer surface, or against the joint head.

An outer surface of the ring, along which the ring is rotatable in the holding element, has a rotationally symmetrical shape. The ring inner surface forms a contact surface with the joint head and at least approximately can form a section of a ball surface. On rotating the clamping element, the contact surface presses against the ball-section-shaped outer surface of the joint head.

Thus, in the region of the ring inner surface and of the joint socket with regard to the joint head two or three contact regions that project inwards with respect to the remaining points of this region are present, and/or two or three contact regions that project outwards with respect to the remaining points of the ball surface are present on the ball surface.

In one embodiment, the eccentric ring is rotatably arranged on the fastening element and on rotation of the eccentric ring with respect to the fastening element, the eccentric ring itself or an intermediate element moved by the eccentric ring is pushed against the joint inner surface, or against the joint socket.

According to different embodiments, for example, two of the defined contact locations arise at two corresponding contact regions by way of deformation of the eccentric ring, in particular on two sides or ends (considered along the periphery) of a flexurally weak location running along the periphery of the eccentric ring. The embodiments described with regard to the invention at other places and with projecting contact regions on the eccentric ring can basically also be realised with this variant with a deformation of the eccentric ring.

According to different embodiments, the joint inner surface has exactly two or exactly three inwardly projecting contact regions, and the ball surface no outwardly projecting contact regions. These contact regions of the joint inner surface can be formed on the ring and/or on the joint socket, wherein the total number of the projecting contact regions should be smaller or equal to three or four or five.

It is generally advantageous if the defined contact locations which can be formed according to the different embodiments, considered in a projection in a plane, in which the holding element extends, are distributed at least approximately uniformly on the joint surfaces of the ball joint.

Generally, for example, the following combinations of contact regions and contact locations resulting therefrom are possible:

1. Three projecting contact regions on the ring, no projecting contact region on the joint socket. On clamping, depending on inaccuracies due to tolerance, a contact location of the joint socket will absorb the clamping force that is introduced through the three projecting contact regions on the ring into the joint head. A situation then sets in between this contact location and the two contact regions of the ring that lie opposite this contact location, as also results in the following combination, i.e. on clamping the result is that two contact locations are present on the ring and one contact location on the joint socket.
2. Two projecting contact regions on the ring, no projecting contact region on the joint socket. The two contact regions on the ring, on clamping, press the joint head against a contact location that, on the bisector of the connection lines of the two contact regions to the center of the joint head, lies opposite the two contact regions. The location of this contact location, thus when the ring is in the clamping position, is defined by the position of the two contact regions and with the two contact regions forms the three-point connection between the joint socket/ring and joint head. The result is therefore that two contact locations are present on the ring and one contact location on the joint socket.
3. Two projecting contact regions on the ring, one projecting contact region on the joint socket. The latter is to be arranged at a location where the contact location described above lies. The result therefore is that here too, two contact locations are present on the ring and one contact location on the joint socket.
4. One projecting contact region on the ring, two projecting contact regions on the joint socket. Analogously to the third combination, the one contact location is to be arranged on the ring where the bisector of the connection lines of the two contact regions of the joint socket to the center of the joint head passes through the ring inner surface at the opposite side. The result is, therefore, two contact locations on the joint socket and one contact location on the ring.
5. No projecting contact region on the ring, two projecting contact regions on the joint socket. Analogously to the second combination, the one contact region on the ring lies where the bisector of the connection lines of the two contact regions of the joint socket to the center of the joint head passes through the ring inner surface at the opposite side. The result is, thus, that here two contact locations are also present on the joint socket and one contact location on the ring.
6. No projecting contact region on the ring, three projecting contact regions on the joint socket. Analogously to the first combination, as to which pair of the three contact regions of the joint socket firstly meets a contact location on the ring inner surface is down to chance. The situation according to the preceding combination then results with this pair, thus two contact locations on the joint socket and one contact location on the ring.

With all combinations, in each case a further variant exists, in that the three contact regions or contact locations which accommodate the clamping force do not lie on a plane through the center of the ball surface. In this case, the location of the contact location, which is defined by two opposite, projecting contact regions, in each case lies in a plane that leads through the respective angle bisector and runs normally to the connection line of the two projecting contact regions. It can happen that the joint head slips on one or more of these contact regions or contact locations, until a fourth contact location results. Even then, it can result that a fourth contact locations arises given an increasing clamping of the elements and with a deformation of at least one of the elements. With a fourth contact location, the distribution of the contact locations can be such that two contact locations are present on the ring and two contact locations on the joint socket; or one contact location is present on the ring and three contact locations on the joint socket The contact regions on the ring can be arranged such that the connection lines of the two contact regions to the middle axis of the eccentric ring form an angle of less than 180° if one contact location is present on the ring; and form an angle of less than 170° and in particular less than 100° if two contact locations are present on the ring.

The contact regions on the joint socket can be arranged essentially uniformly on the periphery of a lead-through (opening) for the fastening element, wherein the lead-through is led through the holding element and the joint socket.

In one embodiment, the eccentric ring is rotatably arranged on the fastening element, and the joint head comprises an intermediate element which can be pressed against the joint socket of the holding element by way of rotating the eccentric ring and, by way of this, forms a first contact location and locks the ball joint. Thereby, the joint head comprises at least two segments that are arranged lying opposite the intermediate element with respect to the joint head, wherein each of the at least two segments defines a contact region and thus establishes a further contact location of the ball joint. Thus, the ring does not contact the holding element, but rather only presses against the holding element via the intermediate element. Thus, again three (or for example four) contact locations are unambiguously defined.

Conversely, according to an analogous embodiment, the eccentric ring is rotatably arranged on the holding element and the holding element includes an intermediate element which, by way of rotating the eccentric ring, can be pressed against the ball surface of the fastening element and, by way of this, forms a first contact location and locks the ball joint. Thereby, the joint socket includes at least two projecting contact regions, which are arranged lying opposite the intermediate element with respect to the center of the joint socket, wherein each of the at least two projecting contact regions defines or establishes a further contact location of the ball joint. Thus, the ring does not contact the fastening element, but rather only presses against the fastening element via the intermediate element.

In one embodiment, the eccentric ring is rotatably arranged on the fastening element and a section of the eccentric ring can be pressed against the joint socket of the holding element by way of rotating the eccentric ring and, by way of this, forms a first contact location and locks the ball joint. Thereby, the joint head comprises at least two segments which are arranged lying opposite the first contact location with respect to the joint head, wherein each of the at least two segments defines a contact region and thus establishes a further contact location of the ball joint. Again three (or for example four) contact locations are unambiguously defined in this way.

The ball joint can be realised by way of the joint head as well as the joint socket—with the exception of the contact regions—comprising spherical surfaces that match one another. In a further embodiment of the invention, the joint socket is spherical only in a part-region, and in a remaining region is designed in a manner opening towards the clamping element, for example conically. The part-region thereby lies at the side of the holding element that lies opposite the clamping element, and the remaining region lies between the part-region and the clamping element. In a further embodiment, the joint socket is designed to be completely open towards the clamping element, preferably conically. A ball joint connection is also formed with the joint socket in the second and the third embodiment of the invention on account of the spherical shape of the joint head, and the projecting contact regions can be arranged accordingly.

According to a further embodiment, the joint socket is only formed by three contact regions, and no other points of the joint socket ever come into contact with the joint head.

In one embodiment, the fastening element is designed in an essentially rotationally symmetrical manner with respect to a longitudinal axis of the fastening element, wherein a plane, which leads through the three defined contact locations, does not contain this longitudinal axis. If indeed this longitudinal axis were to be in this plane, which lies normally or approximately normally to the plane of the holding element, then the distance between individual ones of the contact locations would be limited by the thickness of the holding element. In turn, the holding moment would be relatively low due to the proximity of the contact locations. The mentioned plane of the contact locations can be as parallel as possible to the plane of the holding element, in order to achieve an as high as possible holding moment on locking the ball joint. This, if the ring is attached on the holding element, is essentially also the plane of the ring or the ring plane (expressed more precisely: a plane that lies normally to the rotation axis of the eccentric ring in the holding element).

In one embodiment, the holding element extends in a plane, and a plane that leads through the three defined contact locations has an angle of maximal 45 degrees to the plane of the holding element or to the ring plane of the eccentric ring.

In one embodiment, the smallest distance between the three defined contact locations is at least 0.8 times the diameter of the joint head.

In one embodiment, the holding element or the fastening element (depending on whether the eccentric ring is arranged on the holding element or fastening element) includes a lock-in element for the locking-in (engaging or snap-in) retention of the eccentric ring with regard to a rotation with respect to the holding element or fastening element. With this, the eccentric ring can be delivered and held in an "open" position and does not firstly need to be brought into this position on application of the fastening element. The lock-in element can be a prominence on one of the participating elements, or can be a separate part. The ring, for example, yields elastically on release of the ring from the locked-in position.

The outer side of the clamping element can include a shoulder and/or a cone, which corresponds to the shape of an annular groove in the holding element. The clamping element can include one or more guides, which are suitable for the engagement of the tool, in order to carry out a clamping movement. This, for example, is one or two or more undercut openings for inserting a tool for rotating the eccentric ring.

One or more joint sockets with corresponding annular grooves are formed on the surgical holding element.

Basically, the described fastening device can also be applied in other applications, such as, for example, in engineering, for mountings and stands and likewise. For example, the fastening device can be applied in wood construction or generally with the connection of parts that are to be bonded to one another, by way of two parts after applying an adhesive being screwed to one another by way of the fastening device and being pulled against one another with a bias. The elements of the fastening device can be removed after the bonding has hardened and is stable.

A tool, for example for fixing, locking and releasing a fastening device as described above includes:
an inner shank with an inner tool tip,
an outer shank with an outer tool tip,
wherein the inner shank is arranged within the outer shank and is displaceable with respect to the outer shank along a longitudinal axis of the two shanks.

In one embodiment, the tool can be disassembled or broken down into at least two units without the use of any tool, by way of at least the inner shank and further parts connected thereto, as a first unit, being able to be separated from the outer shank and further parts connected thereto, as a second unit, and these being able to be connected again, without the use of a tool.

In one embodiment, the tool can be disassembled by way of the two units being separable from one another, by way of first bringing the two units into a certain position by way of a displacement along a longitudinal axis of the tool, and the two units then being able to be pulled from one another after rotation about the longitudinal axis.

In one embodiment of the tool tips is designed to hook with an element to be rotated therewith, wherein the shank corresponding to the tool tip is designed in a flexible and rotationally stiff manner. The tool cannot slip on applying a torque if the tool tip is hooked with the element to be rotated. This is important and advantageous with surgical work. The disadvantage, however, thereby can be the fact that a tilting of the longitudinal axis of the tool can exert a moment onto the element to be rotated. The flexible section of the shank is envisaged for precisely this reason.

In one embodiment of the tool, it is the outer tool tip that is formed to hook with an element to be rotated therewith, and thus it is the outer shank that is designed in a flexible and rotationally stiff manner in an elastic region. Either the inner shank itself should also be flexible, or space should be left for the bending of the outer shank, in the same region along the length of the outer shank, so that the outer shank can bend. The latter, for example, can be effected by the inner shank being pulled so far inwards that this region is completely free, or by way of the inner shank having a tapering at the location of this elastic region, when the outer shank is in the operating position.

In one embodiment of the tool, it comprises an asymmetrically acting torque limiter, in particular for the outer shank

BRIEF DESCRIPTION OF THE DRAWINGS

The subject matter of the invention is explained in more detail hereinafter by way of preferred embodiment examples which are represented in the accompanying drawings. In each case are shown schematically in:
FIGS. 6-11 show a fastening device and its individual parts in an embodiment with contact regions on the holding element;
FIGS. 12-15 show an embodiment with contact regions on the joint head;
FIGS. 16-19 show an embodiment with contact regions on the joint head;
FIGS. 20-24 show a fastening device with a screw ring.

DETAILED DESCRIPTION OF THE INVENTION

Figure 1:
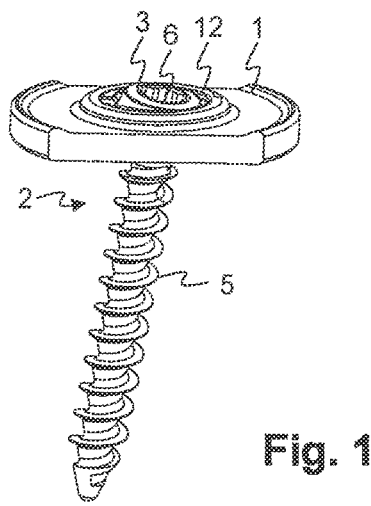
FIGS. 1-4 show a fastening device and its individual parts, with contact regions on the ring.

Basically, the same parts or equally acting parts are provided with the same reference numerals in the figures.

Figure 2:
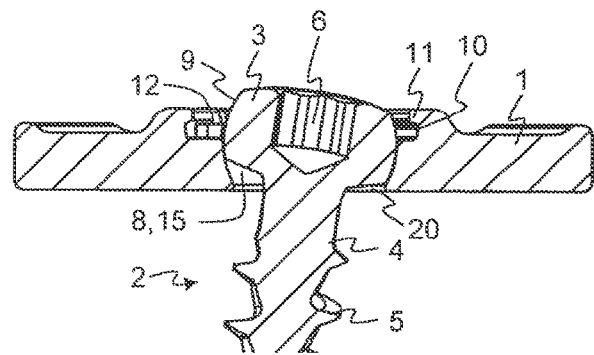

FIG. 1 shows a fastening device with a holding element 1, a fastening element 2 as well as with a clamping element 12. FIG. 2 shows the different elements in a sectioned drawing. The fastening element 2 with a joint head 3 is applied in a holding element 1, which includes a receiver for the fastening element 2 with a joint socket 8. The fastening element 2 includes a receiver 6 for a tool, as well as a shank 4. The shank 4 leads through a lead-through 20 (opening) of the holding element 1. It is provided, for example, with a thread 5 and can be screwed into a substrate to be fixed or stabilised, for example into a bone. The fastening element 2 is rotatably movable in the holding element 1 by way of the ball joint established by the joint socket 8 and joint head 3. The holding element 1, however, is not transitorily movable along the fastening element 2. The ball joint can be locked or fixed by way of a clamping element or a ring 12. The ring includes an opening 17 as well as, lying opposite, a flexurally weak location 17, and these are provided for a simplified assembly of the ring 12 into a peripheral annular groove 10 of the holding element 1.

Figure 3A:
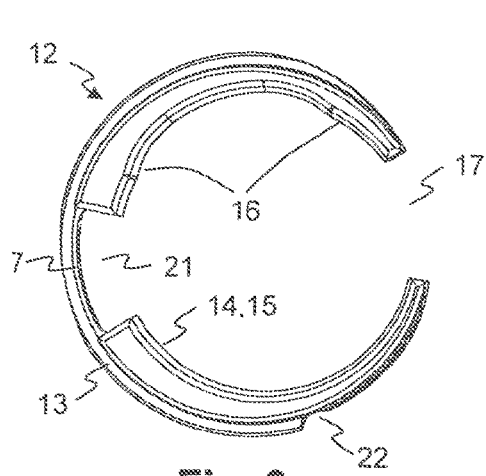
Figure 3B:
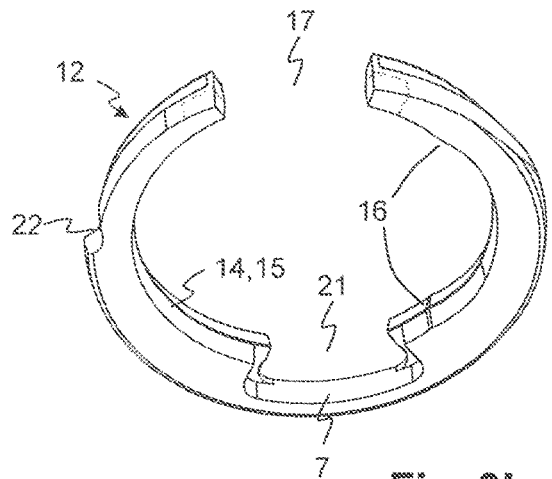
Figure 4:
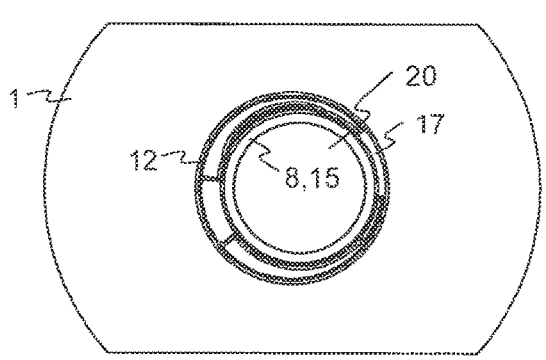

FIG. 3 shows the ring 12 alone in two different views 3a and 3b, and FIG. 4 shows the ring 12 inserted into the holding element 1. A widening and a pressing-together or contraction of the ring 12 is rendered possible by way of the opening 17 on the clamping element or ring 12. Thus, the clamping element 12 can be pressed together and inserted into the annular groove 10. The clamping element 12 is secured from jumping out by way of a shoulder 13 on the ring and by way of a matching shoulder 11 on the annular groove 10. Instead of the shoulder or additionally, the ring 12 and the annular groove 10 can also be designed conically in a manner corresponding to one another. Contact regions 16 are present on the ring inner surface 14, and project inwards with respect to the other regions of the ring inner surface 14, which are part of a ball inner surface 15 for mounting the joint head 3.

The basic manner of functioning of the locking is described in detail in the initially mentioned WO 2010/121388 A1. For example, the annular groove 10 is arranged eccentrically with respect to the center of the joint head 3 and, as the case may be, also with respect to a longitudinal axis of the fastening element 2. The center of a ring inner surface 14 of the clamping element 12 displaces by way of rotating the clamping element 12, and thus locks the joint head 3 with respect to the joint socket 8 or releases it.

The following applies to all embodiments: The combination of joint socket 8 and ring inner surface 14 of the clamping ring 12 forms a joint shell (socket) with an inner surface or joint inner surface, which can be a ball inner surface 15, in which the joint head 3 is mounted. Clearly defined regions, on which a clamping force is exerted onto the joint head 3 on clamping the ring 12, are present by way of the ring inner surface 14 and/or the joint socket 8 including projecting contact regions 16. These regions define at least three points, on which the joint head 3 is held, and thus its orientation is unambiguously defined.

It is the case for the embodiment of FIGS. 1-4 that the projecting contact regions 16 first come into contact with the ball surface 9 of the joint head 3 before the other regions of the ring inner surface 14, and exert a force onto the joint head 3. The joint head 3 is pressed against an oppositely lying point of the joint inner surface or ball inner surface 15 on the joint socket 8 by way of this, and this point forms a third point as a further contact location for fixing the joint head 3. In the case that the joint head 3 slips at this point (wherein, for example, it is rotated about a connection line of the two contact regions 16) the joint head can abut against a fourth point of the ball inner surface 15, which finally limits the movement of the joint head 3. The orientation of the joint head 3 and thus of the fastening element 2 is securely defined and is fixed at the contact regions or contact locations by the clamping force, with this fixation via three or at the most four points (pronounced contact regions and contact locations resulting therefrom).

Figure 5:
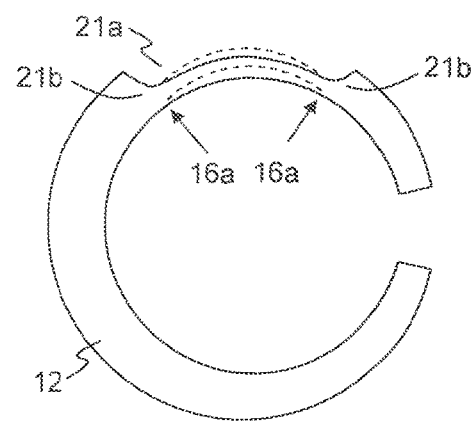
FIG. 5 shows an alternative embodiment of a clamping ring.

FIG. 5 shows a ring 12 in another embodiment. This comprises an outer opening 21a, and accordingly, a thinner, flexurally weak region of the ring (with regard to bending within the plane of the ring). The outer opening 21a thus projects from the outside in the direction of the center of the ring into this. This can be a regular joint inner surface or ball inner surface 15 without projecting prominences. The ring 12 in the flexurally weak region is not supported by the flank of the annular grove 10 in the holding element and deforms outwardly (represented in a dashed manner in FIG. 5, and for a better overview with a greatly exaggerated deformation), on clamping the ring 12 between the holding element 1 and the fastening element 2 (not represented in FIG. 5). The greatest pressing forces between the joint head 3 and the inner surface 14 of the ring 12 occur in transition regions 21b, in which the flexurally weak location begins or ends. This corresponds to two further contact regions 16a, which thus clamp and hold the joint head 3, together with an oppositely lying contact location on the holding element 2 that results from this, at three points. The position of the two contact regions 16a as well as of the oppositely lying contact location on the holding element 2 is thus unambiguously defined by the position of the transition regions 21b on the ring 12.

FIG. 6 shows a fastening device in a further embodiment, FIG. 7 in a sectioned drawing. The elements with regard to their shape and function are basically the same, with the difference that no projecting contact regions 16 are present on the ring 12, but projecting contact regions 16 are present on the holding element 1 on the joint socket 8 as part of the joint inner surface or ball inner surface 15, for example in the region of the lead-through 20. FIG. 8 shows a plan view from the side of the joint socket 8 onto the holding element 1, with an inserted ring 12, and FIG. 9 the same view without the ring 12. FIG. 10 shows a view from below, i.e. from the side of the lead-through 20. FIG. 11 shows a cross section through a holding element 1 with an inserted ring 12.

A lock-in (detent) element 19 projects into the annular groove 10 and engages into a corresponding recess 22 on the shoulder of the ring 12 (see FIGS. 3a and 3b). The lock-in element as drawn can be realised by an inserted pin for design reasons, but according to other embodiments can also be shaped in a pronounced manner as part of the annular groove 10 on the holding element 1. Depending on the design of the recess, the ring can lock in and be held in a defined position, in which the fastening element 2 can be inserted without further ado and/or the rotation movement of the ring 12 can be limited to a predefined region, by way of the cooperation of the lock-in element 19 and the recess on the ring. Such a lock-in element 19 can of course be realised also with the embodiments of FIGS. 1-4.

The opening 17 and/or a further opening 21 of the ring 21 can be designed in an undercut manner, and then a tool for rotating the ring 12 can be introduced into the opening 17, 21 and by way of rotation about the rotation axis of the ring 12 can be hooked with this ring. This means, for example, that the region, through which the tool is inserted into the opening 17, 21, is smaller than a region of the opening 17, 21, which lies further inwards. The tool thus does not slip out of the opening 17, 21 with a pulling force along the axis of the fastening element or the tool. The tool is held back by sections of the ring that project over a part of the opening 17, 21. The flanks of these sections can be obliquely shaped, so that the tool is pulled into the opening 17, 21 on rotating the tool about the axis. This analogously applies to one or more further sections of the ring 12, for example for a further opening 21 lying opposite the opening 17, 21, in the region of the flexurally weak location, as is visible in FIG. 3b. The position of undercut regions on both sides of the opening 17 is indicated by way of dotted lines in FIG. 3b. Such an undercut opening 17, 21 can be realised with the embodiments of FIGS. 1-4 as well as FIGS. 5-10.

It is analogously the case with the embodiment of FIGS. 6-11 that the projecting contact regions 16 on clamping come into contact with the ball surface 9 of the joint head 3 before the other regions of the joint socket 8, and exert a force on the joint head 3. The joint head 3 is pressed against an oppositely lying point of the joint inner surface or ball inner surface 15 on the ring inner surface 14 by way of this, the point forming a further contact location for fixing the joint head 3. The orientation of the joint head 3 and thus of the fastening element 2 is securely defined way with this fixation via three or at most four points (projecting contact regions and contact locations resulting therefrom), and is fixed by way of the clamping force on the contact regions or contact locations.

FIGS. 12 to 15 show different views and sections of an embodiment with contact regions on the joint head, wherein the ring 12 is rotatably arranged on the joint head 3. The joint inner surface 15 of the joint socket 8 can be a regular spherical inner surface without projecting prominences. The ring 12 is an eccentric ring and is rotatably arranged about a middle part 43 of the joint head 3, about an axis which is eccentric, thus is not identical to the longitudinal axis of the fastening element 2, and does not lead through the center of the ball joint. The joint head 3 comprises three segments 42, of which one, hereinafter indicated as intermediate element 41, can be shaped such that it is elastically more yielding (pliant) than the other segments with respect to radial forces. The three segments 42, 41 are arranged distributed roughly uniformly about the periphery of the joint head 3, outside the ring 12 in the radial direction. Their shape at their outer sides corresponds to the ball surface 9 of the joint head 3. On rotating the ring 12, a section of increasing thickness of the ring 12 can be pushed between the middle part 43 and the intermediate element 41, by which means the intermediate element 41 is pressed outwards in the radial direction and against the joint inner surface 15 of the holding element 1. The joint head 3 is clamped in and locked between the intermediate element 41 and the other two segments 42 by way of this. Three projecting contact regions 16 which define the contact locations on the joint are thus defined by the outer sides of the segments 42 and of the intermediate element 41.

FIGS. 16 and 19 show different views and sections of another embodiment with contact regions on the joint head, wherein the ring 12 is rotatably arranged on the joint head 3. The joint inner surface 15 of the joint socket 8 can be a regular spherical inner surface without projecting prominences. The ring 12 is an eccentric ring and is rotatable about a middle part 43 of the joint head 3, about an axis which is eccentric, thus not identical to the longitudinal axis of the fastening element 2 and does not lead through the center of the ball joint. The joint head 3 includes two relatively short segments 42. The two segments 42 are arranged at two of three locations, which are distributed roughly uniformly about the periphery of the joint heed 3, outside the ring 12 in the radial direction. At their outer sides, the shape of the segments 42 corresponds to the ball surface 9 of the joint head 3. A contact location can be formed on the third of the mentioned three locations, between the ring 12 and the joint inner surface 15 of the joint socket 8. For this, a section of a greater thickness of the eccentric ring 12 can be pressed against the joint inner surface 15 by way of rotation of the ring 12. The joint head 3 is clamped and locked between this contact location and the other two segments 42 by way of this. Two projecting contact regions 16 are thus formed by the outer sides of the two segments 42. They define three contact locations on the joint: these on the one hand are the two contact regions 16 and on the other hand the location on the ring 12, the location lying opposite the two contact regions 16 or segments 42.

The shortened segments 42 of the embodiment of FIGS. 16-19 can also be used in the embodiment of FIGS. 12-15, and conversely, the larger segments 42 of the embodiment of FIGS. 12-15 in the embodiment of FIGS. 16-19. With the embodiments of FIGS. 12-19, the joint socket 8 can comprise projecting contact regions 16 as with the embodiment of FIGS. 6-11.

FIGS. 20-24 show a fastening device, in which a screw ring 12*a* is rotatably arranged on the joint head 3. The screw ring can be rotatable about an axis through the center of the ball joint, thus in a non-eccentric manner with respect to the joint head 3. The joint head 3 in the peripheral direction comprises several segments 42 which are separated from one another by slots and by way of this can be pressed outwards. An inner side of the segments 42 (seen in the radial direction) is conically shaped, and the screw ring is shaped as a corresponding outer cone on its outer periphery. The segments 42 are pressed outwards and against the joint socket 8 by way of screwing the screw ring 12*a* onto the middle part 43, by which means the joint is locked.

Sections of a surgical holding instrument 1 are shown in each case in FIGS. 1-24. A complete surgical holding element 1 preferably includes several receivers for fastening elements 2. Embodiments with only one joint could be applied with applications on the vertebral column.

Figure 25:
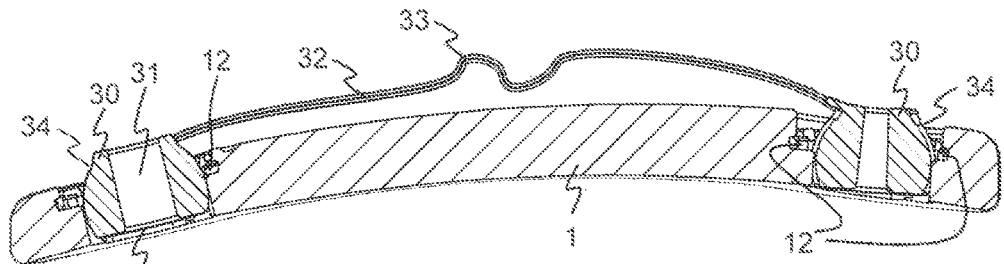
FIGS. 25-27 show drill sleeves for use in the fastening device.
Figure 27:
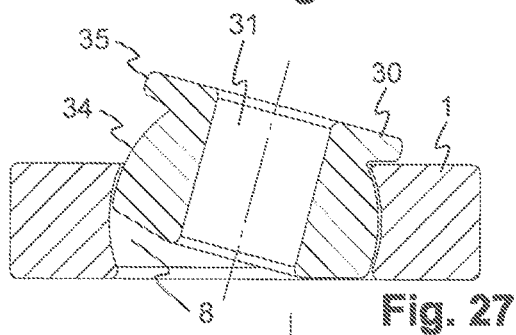
Figure 26:
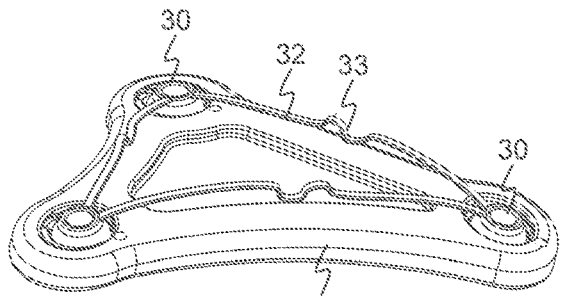

FIGS. 25 and 26 show drill sleeves 30 for use in the fastening device, in a front view and in section. A drill sleeve 30 includes a cylindrical guide opening 31 for guiding a drill. An inner diameter of the guide opening thus corresponds to an outer diameter of the intended drill. The drill sleeves 30 are shaped the same as the joint heads, with an outer ball surface 34, at the outer side, and thus, with the joint socket 8 and the ring 12, form a ball joint. Thus, this ball joint can also be locked by rotating the ring 12. Several drill sleeves 30 can be connected to one another with connection elements or connection ribs 32. These connection ribs 32 form a loss prevention and permit a simple handling of a set of drill sleeves 30. The connection ribs 32 can be formed of an elastic material and can include compensation regions 33, so that the drill sleeves 30, per se, can be moved, in particular for setting their orientation in the joint sockets 8. The drill sleeves 30, for example, are manufactured from a resorbable material that can be broken down in the body, so that swarf or wear arising on drilling is of no problem. FIG. 27 shows a drill sleeve 30 with an abutment 35, which limits the rotation of the drill sleeve 30 in the joint socket 30. The abutment 35 can be a projecting ring or several projecting elements, which are arranged in a ring-like manner and which are arranged in a plane normal to the axis direction of the guide opening. They limit a rotation of the drill sleeve to a maximal angle deviation from a normal to the surface of the holding element 1 by way of this.

The drill sleeves 30 are used for guiding a drill for the pre-drilling of holes, typically in a bone, before the insertion or screwing-in of the fastening elements or screws 2. For this, the drill sleeves 30 can be applied into the holding element 1 before use or can be delivered already in an inserted manner. The drill sleeves 30 can be orientated according to requirement already before the insertion of the holding element 1, and then be locked by way of the ring 12. The holding element 1 is then brought into the desired end position with respect to the bone to be held, and the bores are created in the bone with the help of the drill sleeves 30. The respective drill sleeve 30 can thus be removed if the respective fastening element 2 is to be inserted after the drilling of a hole, before the other holes are drilled. Thereby, the connection ribs 32 to other, still inserted drill sleeves are cut through or severed or are broken away for example at a breakage location (not shown).

A tool as is represented in the FIGS. 28 to 31 in different sections and views can be used for work with the fastening device, i.e. for rotating and in particular for screwing the fastening element 2 and for rotating and thus locking or unlocking the ring 12. The tool as two main constituents comprises:

an inner shank 103 with an inner tool tip 117. This, for example, is shaped corresponding to the receiver 6 of the fastening element 2. The inner tool tip 117 can thus be shaped according to common types of screwdrivers, such as a slot screwdriver, cross-head screwdriver, Philips screwdriver, Pozidriv, hexagonal or Torx screwdrivers. The inner shank 103 is assembled on a grip 109.

an outer shank 114 with an outer tool tip 116, which can be shaped in a manner corresponding to the opening or openings 17, 21 of the ring 12, for example in an undercut manner, so that the outer tool tip 116 hooks in the opening or openings 17, 21, by which means a slipping of the tool is prevented and a secure force transmission or torque transmission on the ring is possible. The outer shank 114 is assembled on a telescopic sleeve 107.

The outer shank 114 and the telescopic sleeve 107 are displaceable with one another with respect to the inner shank 103 and the grip 109, along a longitudinal axis, thus in the axial direction. The inner shank 103 thereby runs within the outer shank 114, for example in a coaxial manner. The outer shank 114 in a first displacement position (FIG. 28) is retracted, so that the inner tool tip 117 can be used. The outer shank 114 is extended or pulled out in the second displacement position (FIG. 29), so that the outer tool tip 116 can be used.

A locking element 106 is provided for locking in the two displacement positions and a release element 105 which can be actuated by way of a release button 101 (FIG. 31) can be actuated for lifting the locking. The locking element 106 includes a locking head 106a, as well as elastic locking tongues 106b with locking detents 106c at their end. The locking detents 106c lock in from the inside on the rear or front detent grooves 118, 119 of the telescopic sleeve 107. In the first displacement position (FIG. 28) they lock in the front detent groove 118, and in the second displacement position (FIG. 29) in the rear detent groove 118. For releasing the locking, the release button 101 is pushed inwards against the force of a spring 102, by which means the release element 105 in each case with a release finger 105a pushes or slides over the locking tongues 106b and presses the locking tongues 106b inwards, and with this also presses the locking detents 106c inwards and pulls them out of the detent groove.

If this release is effected in the first displacement position (FIG. 28), thus with a retracted outer shank 114, then the telescopic sleeve 107 together with the outer shank 114 is pushed forwards by a spring 110. A brake is provided, so that in the case of an inadvertent actuation of the release button 101 during the work with the inner tool tip 117, the outer tool tip 116 abuts against the plate or the ring, and this brake limits this movement. For this, the inner side of the telescopic sleeve 107, which moves along the locking tongues 106b and the locking detents 106c can comprise a narrowed location or brake location 108 that along the movement direction of the locking tongues 106b is located in front of the rear detent groove 118. If the telescopic sleeve 107 moves to the front, the locking tongues 106b at the braking location 108 abut against the inner side of the telescopic sleeve 107, are pushed inwards and thereby brake the movement of the telescopic sleeve 107, before the outer tool tip 116 gets into the region of the inner tool tip 117. The telescopic sleeve 107 is pushed to the front by hand, until the locking tongues 106b lock in the rear detent groove 118 (FIG. 29), in order to bring the outer shank 114 into the frontmost, completely extend displacement position.

A torque is to be transmitted from the hand grip 109 onto the respectively active tool tip 116, 117 when working with the tool.

If the inner tool tip 117 is active, then the torque is led via the following parts: hand grip 109-screws or pins 123 (not visible in FIGS. 28 and 29)-locking head 106a-pin 104-inner shank 103-inner tool tip 117.

If the outer tool tip 116 is active, the torque is led further departing from the inner shank 103, via the following parts: inner shank 103-slot 120 of the inner shank-pin 111 of the telescopic sleeve 107-telescopic sleeve 107-torque limiter 112-outer shank 114-outer tool tip 116.

The mentioned slot 120 of the inner shank runs in the longitudinal direction of the inner shank 103 such that the pin 111 of the telescopic sleeve 107 projects into the slot 120 irrespective of the displacement position.

The mentioned torque limiter 112 is arranged between the front end of the telescopic sleeve 107 and an end-piece 114a of the outer shank 114. The end-piece 114a is pulled with a sleeve head 113, which is fastened on the telescopic sleeve 107, against the torque limiter 112. Thereby, a sliding element 124 for reducing the friction can be arranged between the sleeve head 113 and the end-piece 114a.

Figure 30:
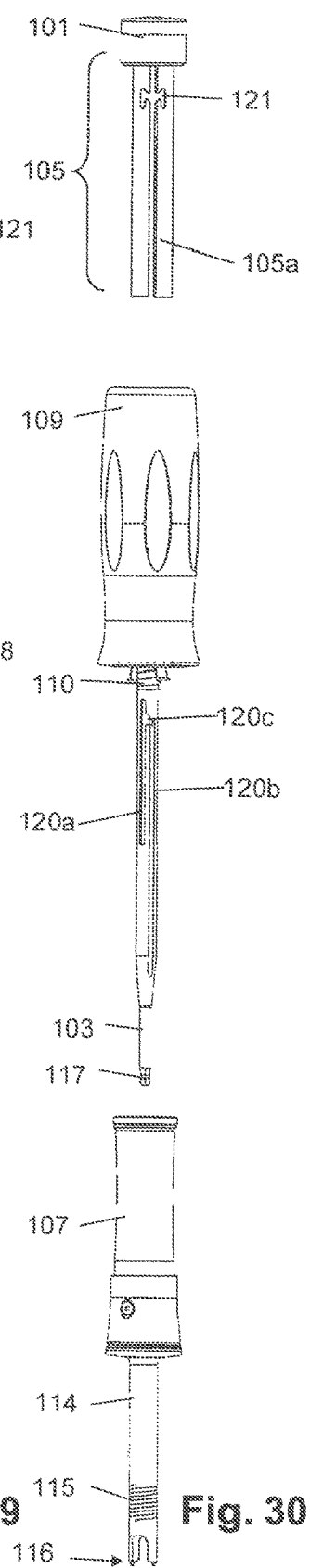
FIG. 30 shows the tool, disassembled for cleaning.
Figure 31:
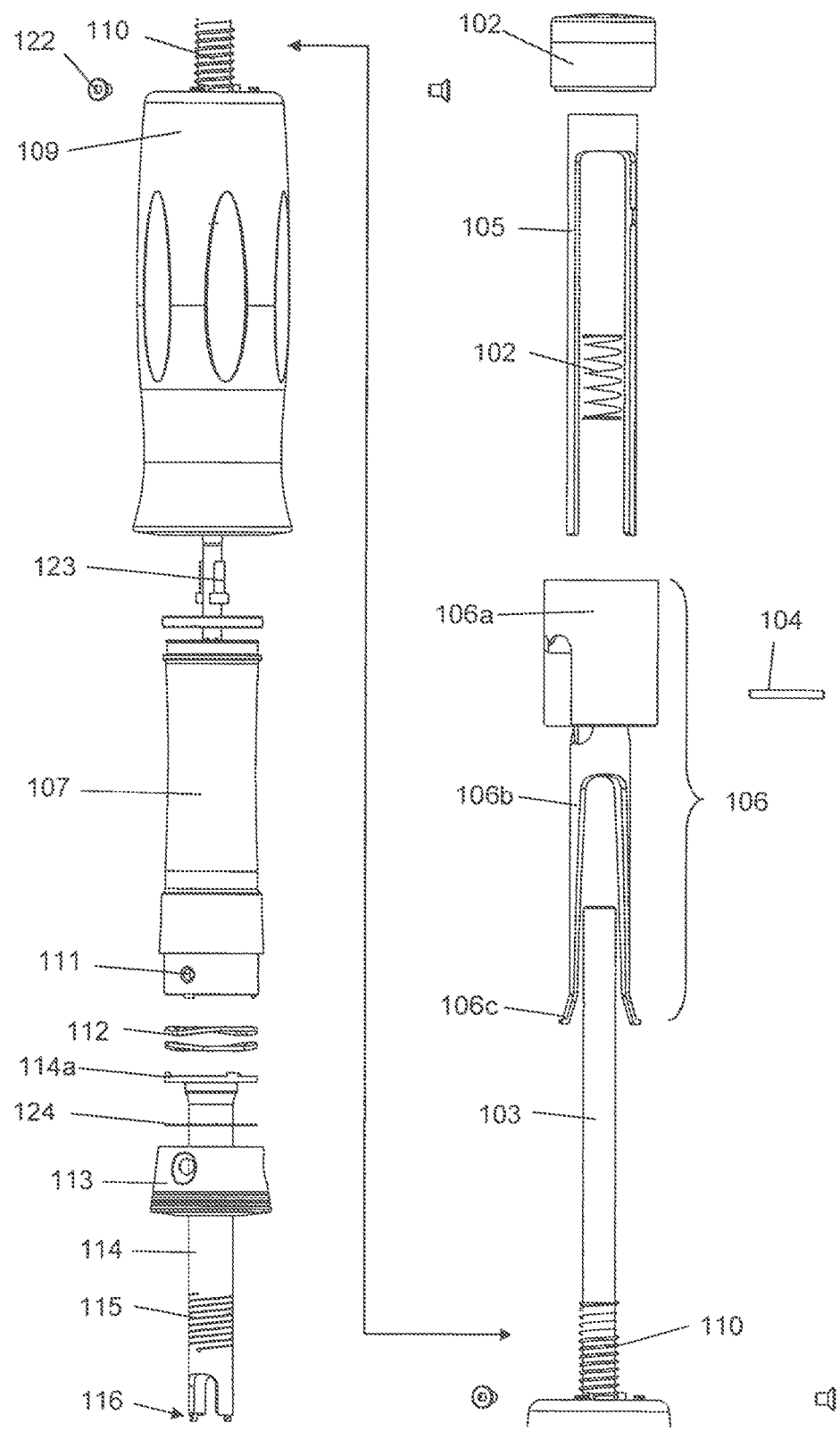
FIG. 31 shows an exploded drawing of the tool.

The tool can be disassembled without any tools, in order to meet hygiene regulations for medically used instruments (FIG. 30). With this, on the one hand the release element 105 with the release head 101 and, on the other hand, the telescopic sleeve 107 with the outer shank 114 can be separated.

In order to separate the telescopic sleeve 107, the slot 120 of the inner shank comprises two sections, in which the pin 111 can slide: a first section 120a for the torque transmission, with a length corresponding to the two displacement positions, and a second section 120b for the disassembly of the telescopic sleeve 107. The two sections 120a, 120b run parallel to one another, offset to one another in the peripheral direction of the inner shank 103. The first section 120a is limited in its length and by way of this limits the movement of the telescopic sleeve 107 along the inner shank 103. The first section 120b, however, leads further to the tip of the inner shank 103 and is open towards the tip. The second section 120b runs into the first one at a transition location 120c. Thus, for disassembly, the telescopic sleeve 107 by way of displacement in the axial direction can be brought into a displacement position, in which the pin 111 lies at the transition location 120c. The telescopic sleeve 107 can then be rotated about the axial direction, by which means the pin 111 gets into the second section and the telescopic sleeve 107 can be pulled off from the inner shank 103. According to one embodiment, moreover the slot 120 at the transition location 120c is not as deep as in the first section 120a, and the pin 111 is pressed into the slot 120 by a spring. Then, on rotation of the telescope sleeve 107, an additional force must be applied, in order to push the pin 111 outwards. This results in a security against inadvertent disassembly.

In order to separate the release element 105, a slot 121 is present in the release fingers, in which slot, for example, the pin 104 projects in the radial direction. On pressing the release element 105, the slot 121 moves along the pin 104, wherein the movement of the release element 105 in the longitudinal direction of the tool is limited by the length of the slot 121. The slot 121 includes a lateral opening, so that the release element 105 is rotatable about the longitudinal axis of the tool when this opening is located at the height of the pin 104, whereupon the release element 105 can be pulled out.

In the previous description, in each case there was mentioned only one slot 120 of the inner shank and one pin 111 running therein. It is to be understood that two, three or more slots 120 and corresponding pins 111 can be arranged or distributed about the periphery of the tool, for an improved force transmission.

Due to the fact that according to one embodiment, the outer tool tip 116 can hook, for example, with a ring 12 of a fastening element 2, and due to the lever arm that the tool forms, large forces can occur on the fastening element 2. This can lead to damage and/or to the displacement of the fastening element or of broken bones connected thereto. So as to prevent this, the outer shank 114 can be designed in a flexible and rotationally stiff manner or include an elastic region 115 that has an increased elasticity, in particular bending elasticity compared to the other regions of the outer shank 114, but is rotationally stiff, in order to be able to transmit a torque. For example, spiral-like incisions or recesses can be present on the outer shank 114 in a manner of a helical coupling, or a helical spring can be installed. The inner shank 103 is designed in a tapered manner at the height of the elastic region 115 (with a pulled-out outer shank) and further to the front, towards the inner tool tip 117, so that the inner shank 103 does not block the bending of the outer shank 114.

Figure 32:
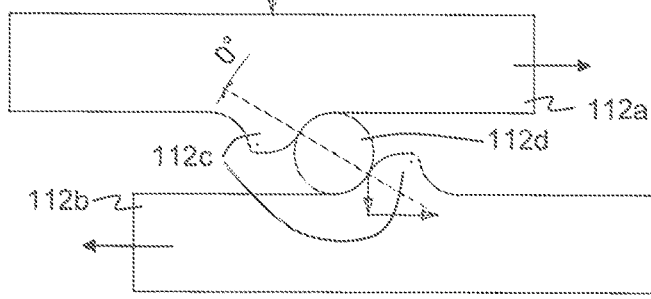
FIGS. 32-34 show a functioning principle of a torque limiter.
Figure 33:
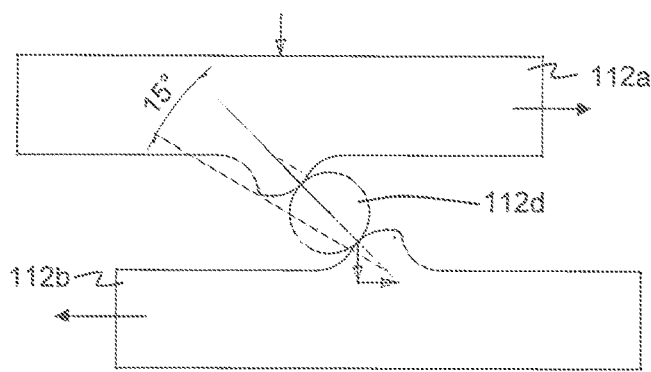
Figure 34:
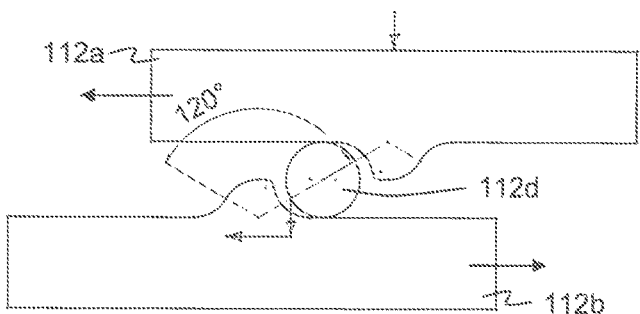
Figure 28:
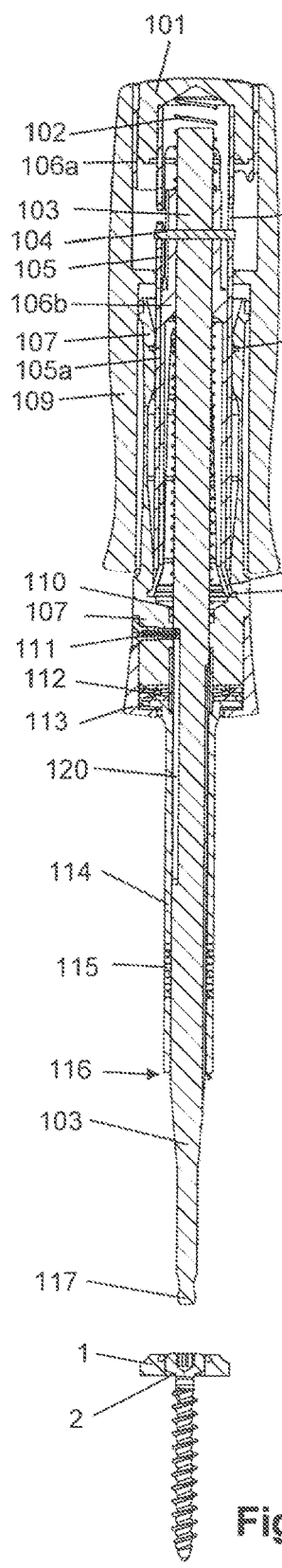
FIG. 28 shows a tool for rotating the ring as well as the fastening element, with a retracted ring tool.
Figure 29:
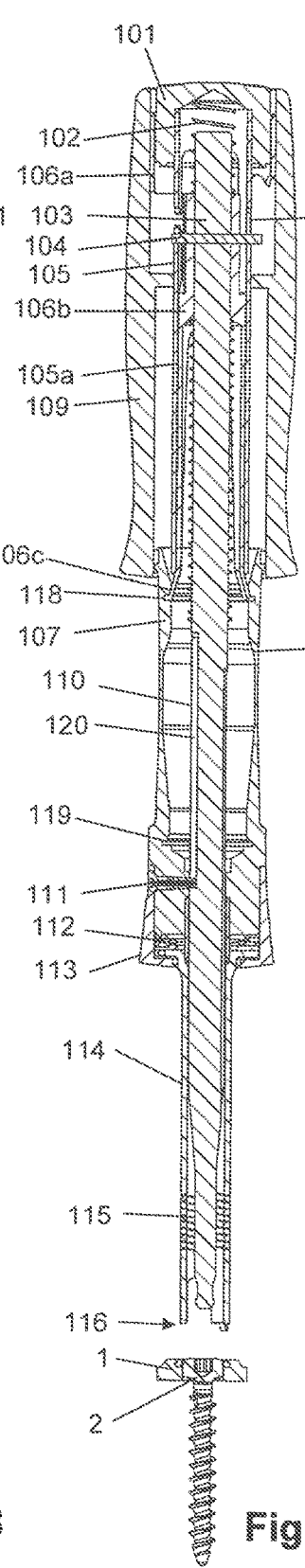
FIG. 29 shows the tool with a pushed forward (advanced) ring tool.

The torque limiter 112 can comprise two resilient elements pressed against one another, which produce a torque due to friction. The FIGS. 32 to 33 alternatively show the manner of functioning of one variant for an asymmetrically acting torque limiter 112. What is shown in each case is a section of an upper ring 112*a* and of a lower ring 112*b* which are pressed against one another by way of a force F in the axial direction, thus parallel to the longitudinal direction of the tool. The two rings 112*a*, 112*b* comprise projections 112*c* which are shaped symmetrically to one another. Several such projections 112*c* are distributed regularly in the peripheral direction about the rings 112*a*, 112*b*. Balls or rollers 11*d* are arranged between the two rings. If the rings 112*a*, 112*b* rotate against one another about the axial direction, then they roll on one another via the rollers 112*d*, until the rollers 112*d* abut on the projections 112*c*. Depending on a steepness of the flanks of the projections, a multiple or a fraction of the force F is to be applied on each projection in the horizontal direction, in order to distance the rings 112*a*, 112*b* to one another. A corresponding maximal torque, at which the torque limiter slips, results from this. The maximal torque in the two rotation directions can be separately selected by way of the different steepness of the flanks at the two sides of the projections 112*c*. With the shown example in FIG. 32, the lifting of the upper ring 112*a* and, thus, the slipping begins with a first torque. In the position according to FIG. 33, the counter-moment produced by the limiter already reduces again according to the course of the profile of the projections 112*c*. With a rotation movement in the opposite direction, the maximal moment required for slippage in the counter direction is significantly higher according to the steeper flank on the opposed side (FIG. 34).

For the described tool, the maximal moment on locking the fastening device (for example by way of rotation in the clockwise direction) is determined by the design and the materials of the fastening device. In contrast, a higher maximal moment is set for unlocking.

The invention claimed is:

1. A fastening device for surgical holding systems, comprising a holding element and a fastening element that are mechanically connectable to one another, and a clamping element,
wherein the holding element comprises a joint socket, and the fastening element comprises a joint head, wherein the joint socket and the joint head are shaped in a manner corresponding to one another and form a ball joint, and movement of the ball joint is lockable by way of the clamping element,
wherein the clamping element is an eccentric ring that, on rotation, clamps the joint head with respect to the joint socket,
wherein the joint socket defines a joint inner surface of the ball joint, and the joint head defines a joint outer surface of the ball joint, the joint outer surface being part of a sphere,
wherein the ball joint is formed by contact between the joint inner surface and the joint outer surface,
wherein the eccentric ring is rotatably arranged on the holding element and on rotation of the eccentric ring with respect to the holding element, the eccentric ring is pressed against the joint outer surface of the ball joint to lock the movement of the ball joint.

2. The fastening device according to claim 1, wherein the ball joint can be locked independently of the position of the fastening element in the holding element.

3. The fastening device according to claim 1,
wherein either the joint inner surface comprises exactly two or exactly three inwardly projecting contact regions, or the joint outer surface of the ball joint comprises exactly two or exactly three outwardly projecting contact regions, and
thereby, when the eccentric ring clamps the joint head with respect to the joint socket but no deformation has taken place on these parts, exactly three or four contact locations are present between the joint inner surface and the joint outer surface of the ball joint.

4. The fastening device according to claim 1, wherein the joint inner surface comprises exactly two or exactly three inwardly projecting contact regions and the joint outer surface of the ball joint comprises no outwardly projecting contact regions.

5. The fastening device according to claim 1, wherein the eccentric ring comprises two projecting contact regions.

6. The fastening device according to claim 5, wherein connection lines of the two contact regions form an angle of less than 170°, in particular an angle of less than 100° to a middle axis of the eccentric ring.

7. The fastening device according to claim 1, wherein two of the three contact locations on two contact regions arise by a deformation of the eccentric ring at two sides of a flexurally weak location which runs along the periphery of the eccentric ring.

8. The fastening device according to claim 7, wherein the flexurally weak location lies opposite to gap in the ring, the gap defining two ends that are spaced apart by the gap.

9. The fastening device according to claim 1, wherein:
the holding element includes a lead-through for the fastening element;
the joint inner surface comprises three projections that project inwardly from a periphery of the lead-through, are arranged on a side of the holding element that lies opposite the eccentric ring, and are arranged essentially uniformly on the periphery of the lead-through.

10. The fastening device according to claim 1, wherein the joint head comprises exactly two or exactly three projections that project outwardly from the joint head and define the joint outer surface of the ball joint; and wherein the joint inner surface has no inwardly projecting contact regions.

11. The fastening device according to claim 1, wherein the eccentric ring is rotatably arranged on the fastening element, and the joint head comprises an intermediate element that can be pressed against the joint socket of the holding element by way of rotating the eccentric ring and by way of this forms a first contact location and locks the ball joint, and the joint head comprises at least two segments that are arranged lying opposite the intermediate element with respect to the joint head, wherein each of the at least two segments defines a contact region and, with this, a further contact location of the ball joint.

12. The fastening device according to claim 1, wherein the eccentric ring is rotatably arranged on the fastening element, and a section of the eccentric ring can be pressed against the joint socket of the holding element by way of rotating the eccentric ring and by way of this forms a first contact location and locks the ball joint, and the joint head comprises at least two segments that are arranged lying opposite the first contact location with respect to the joint head, wherein each of the at least two segments defines a contact region and, with this, a further contact location of the ball joint.

13. The fastening device according to claim 1, wherein the fastening element is designed essentially rotationally symmetrically with respect to a longitudinal axis of the fastening element, and a plane that leads through the three contact locations does not contain this longitudinal axis.

14. The fastening device according to claim 1, wherein the eccentric ring lies in a ring plane, and a plane which leads through the three contact locations, has an angle of maximal 45 degrees to the ring plane.

15. The fastening device according to claim 1, wherein a smallest distance between the three contact locations is at least 0.8 times the diameter of the joint head.

16. The fastening device according to claim 1, comprising a lock-in element for a locking-in fixing of the eccentric ring with regard to a rotation with respect to the holding element.

17. The fastening device according to claim 1, wherein the eccentric ring comprises at least one undercut opening for introducing a tool for rotating the eccentric ring, wherein a first region of the opening through which the tool is inserted is smaller than a second region of the opening engaged by the tool for rotating the eccentric rind.

18. The fastening device according to claim 1, wherein when the eccentric ring clamps the joint head with respect to the joint socket, positions of three contact locations of the ball joint that lock the ball joint are defined by a shape of at least one of the joint socket, the joint head and the eccentric ring, and the three contact locations are present between the joint outer surface of the ball joint and the joint socket or the eccentric ring.

19. A fastening device for surgical holding systems, comprising a holding element and a fastening element that are mechanically connectable to one another, and a clamping element,
   wherein the holding element comprises a joint socket, and the fastening element comprises a joint head, wherein the joint socket and the joint head are shaped in a manner corresponding to one another and form a ball joint, and the movement of the ball joint is lockable by way of the clamping element,
   wherein the clamping element is an eccentric ring that, on rotation, clamps the joint head with respect to the joint socket,
   wherein the joint socket defines a joint inner surface of the ball joint, and the joint head defines a joint outer surface of the ball joint, the joint outer surface being part of a sphere,
   wherein the ball joint is formed by the joint inner surface of the ball joint and the joint outer surface of the ball joint,
   wherein the joint head includes a receiver for engaging a tool used to rotate the fastening element,
   wherein when the eccentric ring clamps the joint head with respect to the joint socket, the receiver is not covered by the eccentric ring such that the receiver is accessible for engaging the tool.

20. A fastening device for surgical holding systems, comprising a holding element and a fastening element that are mechanically connectable to one another, and a clamping element,
   wherein the holding element comprises a joint socket, and the fastening element comprises a joint head, wherein the joint socket and the joint head are shaped in a manner corresponding to one another and form a ball joint, and the movement of the ball joint is lockable by way of the clamping element,
   wherein the clamping element is an eccentric ring that, on rotation, clamps the joint head with respect to the joint socket,
   wherein the joint socket defines a joint inner surface of the ball joint, and the joint head defines a joint outer surface of the ball joint, the joint outer surface being part of a sphere,
   wherein the ball joint is formed by the joint inner surface of the ball joint and the joint outer surface of the ball joint,
   wherein the ball joint can be locked independently of the position of the fastening element in the holding element.

* * * * *